United States Patent [19]

Yu

[11] 4,124,604
[45] Nov. 7, 1978

[54] BIS-[(5-P-CHLOROPHENYL)FURFURYL]A-MINE HYDROCHLORIDE

[75] Inventor: Chia-Nien Yu, Norwich, N.Y.

[73] Assignee: Morton-Norwich Products, Inc., Norwich, N.Y.

[21] Appl. No.: 874,469

[22] Filed: Feb. 2, 1978

[51] Int. Cl.² .................................................. C07D 307/52
[52] U.S. Cl. .................................. 260/347.7; 424/285
[58] Field of Search ...................................... 260/347.7

[56] References Cited
U.S. PATENT DOCUMENTS 4,067,888  1/1978  Pelosi ................................. 260/347.7

*Primary Examiner*—Richard L. Raymond
*Attorney, Agent, or Firm*—Anthony J. Franze

[57] ABSTRACT

Bis-[(5-p-chlorophenyl)furfuryl]amine hydrochloride is useful as an anti-inflammatory agent.

1 Claim, No Drawings

BIS-[(5-P-CHLOROPHENYL)FURFURYL]AMINE HYDROCHLORIDE

This invention is concerned with the chemical compound bis-[(5-chlorophenyl)furfuryl]amine hydrochloride. It possesses anti-inflammatory properties. When administered per os at a dose of 300 mg/kg to rats, inhibition of edema induced by the well-known carrageenin raw paw edema method described by Winter et al. in Proc. Soc. Exp. Biol. Med. 111:544 (1962) was achieved.

The compound of this invention can be readily compounded in a variety of pharmaceutical forms such as tablets, capsules, elixirs, solutions and the like using conventional adjuvants and excipients with which there is no incompatibility.

In order that this invention may be readily available to and understood by those skilled in the art, the currently preferred method for making it is described:

Bis-[(5-p-Chlorophenyl)furfuryl]amine Hydrochloride

A suspension of 10 g (0.04 mole) of 5-(p-chlorophenyl)furfurylamine hydrochloride in about 600 ml of water was warmed on steam bath until almost all the solid dissolved. Then it was made alkaline with sodium hydroxide solution. Brown oil separated. The mixture was extracted with toluene. The toluene extract was washed with water, dried over $MgSO_4$ and concentrated to a brown oil.

The free base was then heated at reflux with 8.5 g (0.04 mole) of 5-(p-chlorophenyl)-2-furaldehyde in 300 ml of methanol. After 2 hrs. of reflux, the solution was allowed to stand. Crystalline solid separated. To this mixture under stirring was added 1.55 g (0.04 mole) of sodium borohydride in about 1 hr. The temperature was maintained around 27°–32° during the addition. The mixture was allowed to stir further at ambient temperature for 1½ hrs. and then heated at reflux on steam bath for an additional 1 hr. The solution was filtered while still warm and the filtrate was concentrated in a water bath at reduced pressure to a pale yellow solid residue. This residue was partitioned in chloroform and water. The chloroform layer was dried over $MgSO_4$ and then concentrated in a water bath at reduced pressure to a brown liquid. Trituration with an isopropanol-HCl solution with slight warming gave a pale greyish solid. The solid was filtered, washed with isopropanol, ether and air dried. The yield was 15.5 g (89%), m.p. 232°–235° D.

Anal. Calcd. for $C_{22}H_{17}Cl_2NO_2 \cdot HCl$: C, 60.78%, H, 4.17%; N, 3.22%. Found: C, 60.58%; H, 4.33%; N, 3.23%.

What is claimed is:

1. Bis-[(5-p-chlorophenyl)furfuryl]amine hydrochloride.

* * * * *